United States Patent
Halperin et al.

(10) Patent No.: US 9,952,200 B2
(45) Date of Patent: Apr. 24, 2018

(54) CELL BASED QUALITY CONTROL BIOASSAYS FOR NUTRICEUTICAL AND MEDICINAL PRODUCTS

(71) Applicant: President and Fellows of Harvard College, Cambridge, MA (US)

(72) Inventors: Jose A. Halperin, Brookline, MA (US); Michael Chorev, Chestnut Hill, MA (US); Huseyin Aktas, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/382,116

(22) PCT Filed: Jul. 22, 2013

(86) PCT No.: PCT/US2013/051433
§ 371 (c)(1),
(2) Date: Aug. 29, 2014

(87) PCT Pub. No.: WO2014/015328
PCT Pub. Date: Jan. 23, 2014

(65) Prior Publication Data
US 2015/0301023 A1    Oct. 22, 2015

Related U.S. Application Data

(60) Provisional application No. 61/674,180, filed on Jul. 20, 2012.

(51) Int. Cl.
*G01N 33/50* (2006.01)

(52) U.S. Cl.
CPC ..... *G01N 33/5011* (2013.01); *G01N 33/5023* (2013.01)

(58) Field of Classification Search
CPC ........... G01N 33/5005; G01N 33/5008; G01N 33/507
See application file for complete search history.

(56) References Cited

FOREIGN PATENT DOCUMENTS

| CN | 101671669 A | 3/2010 |
|---|---|---|
| CN | 102459637 A | 5/2012 |
| WO | 2008/008333 | 1/2008 |
| WO | WO 08/008333 | * 1/2008 |
| WO | 2010/138820 | 12/2010 |
| WO | WO 10/138820 | * 12/2010 |

OTHER PUBLICATIONS

Chen et al, Nat. Chem. Biol. 7(9): 610-616; available online Jul. 17, 2011.*
Hoshino et al, Agric. Biol. Chem. 54(6):1459-1467, 1990.*
Picot et al, Process Biochem. 41:1217-1222, 2006.*
Xu et al, Nature Protocols 4(9)1 338-1349, 2009.*
Weihua et al, Cancer Cell 13:385-393, 2008.*
Agromayor et al, Mol. Cell. Biol. 26(12):4448-4461, 2006.*
Paddison et al, Genes & Devel. 16:948-958, 2002.*
http://www.edvotek.com/Experiments; last accessed Apr. 7, 2017.*
International Search Report for PCT/US2013/051433 dated Sep. 20, 2013.
Chen et al., "Chemical genetics identify eIF2[alpha} kinase heme-regulated inhibitor as an anticancer target", Nature Chemical Biology, 7(9):610-616 (2011).
Denoyelle et al., "In vitro inhibition of translation initiation by,—diarylureaspotential anti-cancer agents", Bioorganic & Medicinal Chemistry Letters, Pergamon, 22(1):402-409 (2011).
Van den Beucken et al., "Regulation of Cited2 Expression provides a functional link between translational response during hypoxia", Radiotherapy and Oncology, Elsevier, Ireland, 83(3):346-352 (2007).
Kaufman et al., "The Phosphorylation State of Eucaryotic Initiation Factor 2 Alters Translational Efficiency of Specific MRNA", Molecular and Cellular Biology, American Society for Microbiology, Washington, US, 9(3):946-958 (1989).
English translation of office action dated Oct. 30, 2015 in corresponding Chinese Patent Application No. 201380031597.X.

* cited by examiner

*Primary Examiner* — Kevin K Hill
(74) *Attorney, Agent, or Firm* — Fish & Richardson P.C.

(57) ABSTRACT

A method for determining the translation initiation inhibitory potency of a composition having an unknown level of translation initiation inhibitory activity which comprises contacting an eI-F2α-WT cell with said composition for a time and at a temperature effective to inhibit proliferation of said cell, measuring the level of inhibition of proliferation of said eIF2α-WT cells induced by said sample and comparing the level of inhibition of proliferation induced by said sample with the level of inhibition of proliferation induced by a standard having a known amount of said activity, the amount of said translation initiation inhibitory activity in said sample being proportional to the level of inhibition of proliferation of said eIF2α-WT cell.

19 Claims, 4 Drawing Sheets

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Kozak consensus sequence

<400> SEQUENCE: 1
gccaccatgg                                                          10
```

CELL BASED QUALITY CONTROL BIOASSAYS FOR NUTRICEUTICAL AND MEDICINAL PRODUCTS

CROSS-REFERENCE TO RELATED APPLICATIONS

This application is a United States national phase application under 35 U.S.C. 371 of International Application Number PCT/US2013/051433 filed Jul. 22, 2013 which claims priority from U.S. provisional patent application No. 61/674,180 filed Jul. 20, 2012, both of which applications are hereby incorporated herein by reference in their entirety.

FIELD OF THE INVENTION

Embodiments of the present invention relate in general to the assay of food, nutriceutical and medicinal products for properties beneficial to human or animal health. Embodiments of the present invention further include improved methods, employing cell based assays using novel cell lines for the assay of such products for activity as inhibitors of translation initiation.

BACKGROUND OF THE INVENTION

Messenger RNA (mRNA) translation initiation plays a critical role in the regulation of cell growth and malignant transformation because expression of most oncogenic and cell growth regulatory proteins is translationally regulated (Flynn et al., 1996, Cancer Surv. 27:293; Sonenberg et al., 1998, Curr. Opin. Cell Biol. 10:268). For this reason, translation initiation is a tightly regulated cellular process. Failure in negative regulation of translation initiation may lead to the induction, onset and progression of cancer (Donze et al., 1995, Embo J. 14: 3828; Rosenwald, 1996, Bioessays 18: 243-50; De Benedetti et al., 2004, Oncogene 23: 3189-99; and Rosenwald, 2004, Oncogene 23:3230). Inhibition of poorly-regulated translation initiation also can cause reversion of transformed phenotypes (Jiang et al., 2003, Cancer Cell Int. 3:2; Graff et al., 1995, Int. J. Cancer 60:255). The eIF2 GTP Met-tRNA, complex (also known as the ternary complex) is a key positive regulator of translation initiation. Limiting its availability curtails initiation of new rounds of protein translation. While translation of many oncogenic proteins and other cell growth factors relies heavily on the ternary complex, the same is not true of housekeeping genes, for which reason food, nutriceutical and medicinal products that help to limit the amount, availability or activity of the ternary complex potentially offer a safe means of preventing and treating disease. In addition, expression of certain tumor suppressors and pro-apoptotic genes and/or proteins actually increases in the presence of inhibitors of the ternary complex or, more generally, of translation initiation. Reduced translation of oncogenic proteins, especially combined with up-regulation of tumor suppressors and pro-apoptotic genes, tends overall to prevent and/or repress the malignant phenotype.

Eicosapentaenoic acid (EPA), an n-3 polyunsaturated fatty acid (n-3 PUFA), is found in large quantities in oil derived from fish, particularly those of wild populations native to cold oceanic waters. Farmed fish typically contain far lower levels of n-3 PUFAs than do wild fish. It has been observed that when marine fish oil is administered to human prostate cancer patients, eIf2α is phosphorylated, suggesting that the availability of functional eIF2 to the ternary complex has been reduced, in accordance with the findings using EPA and synthetic inhibitors of the ternary complex in animal models or cell-based experimental systems. Accordingly, dietary supplements that contain translation initiation inhibitors represent attractive commercial products for treatment and/or prevention of cancer and/or proliferative diseases in which abnormal cell proliferation is a characteristic pathological abnormality. Such dietary supplements can also act as translation initiation regulators, and represent attractive commercial products for treatment and/or prevention of metabolic diseases such as obesity and diabetes.

Fish oil from a variety of sources is widely available to consumers as a food product or nutritional supplement. The oil, or oil-derived fractions or components, contained in different production lots, batches, samples or doses of a product may vary in quality or potency, depending on their sources (e.g., climates, fish species or growth conditions, suppliers) or processing conditions. The same even may be true of the contents of a single lot, batch, sample or dose of product. Other food, nutriceutical or medicinal products that contain natural or synthetic inhibitors of translation initiation can vary in quality or potency for similar reasons.

There is a need for quality control and/or assurance with respect to a product's physiological or medicinal effects on potential consumers.

SUMMARY OF THE INVENTION

Dietary supplements with therapeutic/preventive effects for human diseases represent a fast growing, multibillion dollar industry worldwide. However, a major unresolved problem in this industry is the lack of quality control of products that are extracted from natural sources to assure a specific biological activity and potency, a homogeneity in biological activity among different preparations extracted/produced from the same plant/animal source, and a comparable potency among the preparations extracted from the same plant or animal species but originating from different geographical regions and/or industry sources.

Inhibitors, upregulators or other modulators of translation initiation have broad-spectrum anti-cancer, anti-cell proliferation effects as well as broad-spectrum effects on energy balance. Nutriceuticals containing inhibitors, upregulators or other modulators of translation initiation, including but not limited to fish oil preparations, could be used for prevention of human diseases characterized by abnormal cell proliferation, including cancer. However, the current absence of bioassays to determine the biological activity of nutriceuticals of this kind makes it impossible to control their quality, potency and/or homogeneity among different brands or sources or among different batches or products from a single brand or source.

Accordingly, in certain exemplary embodiments, methods for the quality control and/or assurance of food, nutriceutical and medicinal products with respect to such products' ability to modulate mRNA translation initiation, thereby addressing the need to supply accurate information to consumers regarding the potential health benefits of such products are provided.

Translation initiation-specific bioassays that can be used to quantitatively assess the biological activity of compounds, e.g., nutriceuticals that contain inhibitors, upregulators or modulators of translation initiation are provided. The translation initiation-specific assays provided herein assess the quality (e.g., biological activity), potency and batch homogeneity of nutriceuticals that contain products, e.g., endogenous products or additives that act as inhibitors, upregulators or other modulators of translation initiation.

These assay methods offer accurate and rapid means of determining the extent to which a given sample of a food, nutriceutical or medicinal product can modulate translation initiation, and thereby benefit a human or animal that consumes such product or to whom such product is administered. These assay methods generally permit a sample of such a product to be tested for its ability to inhibit mRNA translation initiation. Exemplary assays described herein enable detection of a sample's ability to inhibit formation, availability or activity of the ternary complex, whether through phosphorylation of eIf2α or otherwise.

In certain exemplary embodiments, a sample of a product may be tested for its ability to upregulate translation of certain mRNA transcripts. Upregulation of translation of such transcripts may indicate the presence, level, availability and/or activity of EPA or other 3-n PUFAs contained in such sample. In certain embodiments, a sample's ability to increase translation of certain mRNA transcripts whose 5' untranslated regions (5' UTRs) contain two or more open reading frames (ORFs) may be detected. In certain embodiments, a sample's ability to increase translation of one or more of ATF-4, BRCA1 mRNAb, CD59, TCTP and GCN4 may be tested as a measure of such sample's potency and/or ability to confer health benefits on a human or animal that consumes the corresponding product or to whom the corresponding product is administered. Such assays may detect increased amounts, availability or activities of proteins made as a result of upregulated translation of these mRNAs. The extent to which translation of marker proteins is increased, upregulated or otherwise modulated may be determined by comparison of test results with controls. Without wishing to be bound by any particular theory, such increased translation may be facilitated by phosphorylation of eIf2α and/or inhibition of the ternary complex.

The invention enables a sample of a food, nutriceutical or medicinal product to be assayed for beneficial activities by detecting nucleic acid products of genes whose transcription is increased, upregulated or otherwise modulated in the presence of EPA or other 3-n PUFAs contained in such sample.

In certain embodiments, the invention provides for the detection of gene transcripts that are increased, upregulated or otherwise modulated in the presence of EPA, other 3-n PUFAs or other beneficial agents. Such transcripts may include, in non-limiting fashion, those that encode ATF-4, BiP, CHOP, Xpb-1 and amino acid synthetases. Certain embodiments of the invention provide for detection of mRNA transcripts that encode such proteins, such as through reverse transcription, nucleic acid amplification (e.g., PCR or isothermal amplification methods known in the art) or nucleic acid hybridization methods. Detection of increased, upregulated or otherwise modulated gene transcription also may be performed using reporter gene assays, e.g., such that the promoter of the gene of interest is operably linked to a reporter gene prior to contact with the test or control sample in a system that permits DNA transcription to occur. The extent to which transcription is increased, upregulated or otherwise modulated is determined through comparison of transcription levels or the reporter gene activity observed in the test sample with those observed for an external or internal (e.g., dual-reporter) standard or control.

Certain exemplary embodiments provide for the assay of food, nutriceutical and medicinal products by detecting proteins encoded by gene transcripts that are increased, upregulated or otherwise modulated in the presence of EPA, other 3-n PUFAs or other beneficial agents. Such proteins may include, in non-limiting fashion, ATF-4, BiP, CHOP, Xbp-1 and amino acid synthetases. Levels of such proteins observed in the presence of a test sample may be compared to those observed in the presence of a standard or other control sample to determine the potency of the test sample.

In another embodiment, a method of determining batch homogeneity of a plurality of individual compositions comprising the steps of detecting translation initiation inhibition, upregulation or other modulation activity of at least one of the individual compositions, and comparing the translation initiation inhibition, upregulation or other modulation activity of the at least one of the individual compositions to a standard to determine batch homogeneity is provided.

Accordingly, in certain exemplary embodiments, a method for determining whether a substance (e.g., a substance derived from fish oil and/or a substance containing EPA) has one or more beneficial biological, nutriceutical or medicinal properties is provided. The method includes the steps of providing a second sample including a second mRNA sequence having at least two open reading frames at its 5' UTR, wherein the second mRNA sequence encodes a second biomarker protein, contacting the second sample with the substance, and detecting translation levels of the first and second biomarker proteins, wherein the translation level of the second biomarker protein is greater than the translation level of the first biomarker if the substance has one or more beneficial biological, nutriceutical or medicinal properties. In certain aspects, the first sample is contacted with a standard substance or a control substance. In other aspects, the first mRNA and the second mRNA have the same sequence. In other aspects, the first biomarker protein and the second biomarker protein are the same protein. In certain aspects, the first and second biomarker proteins are selected from the group consisting of breast cancer susceptibility gene 1 (BRCA1) transcript b product, activating transcription factor 4 (ATF-4), translationally controlled tumor protein (TCTP), protectin (CD59) and general control nonderepressible 4 (GCN4). In other aspects, the step of detecting translation levels is performed by one or more of Western analysis, ELISA and immunocytochemistry. In certain aspects, the sample is an animal, a cell or a cell free system (e.g., a rabbit reticulocyte lysate system) in which DNA transcription and/or mRNA translation, as appropriate, can occur. Cells may be derived from humans, other mammals (including without limitation mice and rats), chickens or other birds or yeast. Cell Free systems include rabbit reticulocyte, wheat-germ, or mammalian cell cytoplasmic extracts such as HeLa S100 extracts. In certain aspects, the 5' UTR is naturally occurring or synthetic. In other aspects, the 5' UTR is operably linked to a coding sequence that encodes a reporter protein. In certain aspects, translation levels are determined by assaying one or more activities of the reporter protein. In other aspects, the translation level of the second biomarker protein is at least 150% of the translation level of the first biomarker. In certain aspects, the substance is being assayed for an n-3 polyunsaturated fatty acid (PUFA) (e.g., an eicosapentaenoic acid (EPA)) activity. In certain aspects, the substance is a food product sample, a nutriceutical product sample or a pharmaceutical product sample.

In certain exemplary embodiments, a method for determining whether a substance (e.g., a substance derived from fish oil and/or a substance containing EPA) has one or more beneficial biological, nutriceutical or medicinal properties is provided. The method includes the steps of providing a sample including an mRNA sequence having at least two open reading frames at its 5' UTR, wherein the mRNA sequence encodes a biomarker protein, contacting the sample with the substance, detecting a translation level of the biomarker protein, and detecting a translation level of an internal standard protein, wherein the translation level of the biomarker protein is greater than the translation level of the internal standard protein if the substance has one or more beneficial biological, nutriceutical or medicinal properties. In certain aspects, the internal standard protein is encoded by an mRNA sequence having one or no open reading frames at its 5' UTR. In other aspects, the biomarker protein is selected from the group consisting of BRCA1 transcript b product, ATF-4, TCTP, CD59 and GCN4. In other aspects, the step of detecting the translation level is performed by one or more of Western analysis, ELISA and immunocytochemistry. In yet other aspects, the 5' UTR is naturally occurring or synthetic. In other aspects, the 5' UTR is operably linked to a coding sequence that encodes a reporter protein. In other aspects, translation levels are determined by assaying one or more activities of the reporter protein. In other aspects, the translation level of the biomarker protein is at least 150% of the translation level of the internal standard. In certain aspects, the substance is being assayed for an n-3 PUFA (e.g., EPA) activity. In certain aspects, the substance is a food product sample, a nutriceutical product sample or a pharmaceutical product sample.

In certain exemplary embodiments, this invention provides a method for detecting whether a substance (e.g., a substance derived from fish oil and/or a substance containing EPA) mediates transcriptional upregulation of a biomarker gene. The method includes the steps of providing a first test system including a mRNA sequence having a coding region for a first reporter protein operably linked to a first biomarker promoter, providing a second test system including a second mRNA sequence having a coding region for a second reporter protein operably linked to a second biomarker promoter, contacting the second test system with the substance, detecting transcription levels of the first and second mRNA sequences, comparing the transcription level of the first and second mRNA's and determining whether the transcription level of the second mRNA sequence is greater than the transcription level of the first mRNA sequence, and identifying the substance as an upregulator of the biomarker gene if the transcription level of the second mRNA is greater than the transcription level of the first mRNA, if the substance mediates transcriptional upregulation of the biomarker gene. In certain aspects of the invention, the first and second test systems are an animal assay, a cell based assay or a cell free assay. In certain aspects, the first test system is contacted with a standard substance or a control substance. In other aspects the first mRNA and the second mRNA have the same sequence and/or the first reporter protein and the second reporter protein are the same protein. In certain aspects, transcription levels are determined by real time PCR (e.g., in vitro or in vivo (e.g., in cells)). In certain aspects, transcriptional activity is determined by detecting one or more reporter protein activities. In other aspects, the biomarker gene encodes a pro-apoptotic protein or a tumor suppressor protein (e.g., CHOP, BiP, ATF-4, Xbp-1, an amino acid synthetase or the like). In certain aspects, transcription of the second mRNA sequence is at least 150% of the transcription level of the first mRNA sequence. In certain aspects, the substance is being assayed for an n-3 PUFA (e.g., EPA) activity. In certain aspects, the substance is a food product sample, a nutriceutical product sample or a pharmaceutical product sample.

In certain exemplary embodiments, the invention provides a method for manufacturing a quality controlled fish oil product. The method includes the steps of providing a first sample including a first mRNA sequence having at least two open reading frames at the 5' untranslated region of the first mRNA sequence, wherein the first mRNA sequence encodes a first biomarker protein, providing a second sample including a second mRNA sequence having at least two open reading frames at the 5' untranslated region (UTR) of the second mRNA sequence, wherein the second mRNA sequence encodes a second biomarker protein, contacting the second sample, comprising the translation levels and identifying with the fish oil product, detecting translation levels of the first and second biomarker proteins, wherein the translation level of the second biomarker protein is greater than the translation level of the first biomarker if the fish oil product can provide one or more beneficial biological, nutriceutical or medicinal properties to a subject, and selecting a fish oil product that has a greater translation level as a quality controlled fish oil product. In certain aspects of the present invention, the first sample is contacted with a standard substance or a control substance. In other aspects, the first mRNA and the second mRNA have the same sequence. In yet other aspects, the first biomarker protein and the second biomarker protein are the same protein (e.g., BRCA1 transcript b product, ATF-4, TCTP, CD59 and GCN4).

In certain exemplary embodiments, the invention provides a method for manufacturing a quality controlled fish oil product. The method includes the steps of providing a sample including an mRNA sequence having at least two open reading frames at the 5' untranslated region of the mRNA sequence, wherein the mRNA sequence encodes a biomarker protein, contacting the sample with the fish oil product, detecting a translation level of the biomarker protein, detecting a translation level of an internal standard protein, comparing and identifying wherein the translation level of the biomarker protein is greater than the translation level of the internal standard protein if the fish oil product can provide one or more beneficial biological, nutriceutical or medicinal properties to a subject, and selecting a fish oil product that has a greater translation level as a quality controlled fish oil product. In certain aspects, the biomarker protein is selected from the group consisting of BRCA1 transcript b product, ATF-4, TCTP, CD59 and GCN4.

In certain exemplary embodiments, the invention provides a method for manufacturing a quality controlled fish oil product. The method includes the steps of providing a first test system including a mRNA sequence having a coding region for a first reporter protein operably linked to a first biomarker promoter, providing a second test system including a second mRNA sequence having a coding region for a second reporter protein operably linked to a second biomarker promoter, contacting the second test system with the fish oil product, detecting transcription levels of the first and second mRNA sequences, comparing and selecting wherein the transcription level of the second mRNA sequence is greater than the transcription level of the first mRNA sequence if the fish oil product can provide one or more beneficial biological, nutriceutical or medicinal properties to a subject, and selecting a fish oil product that has a greater translation level as a quality controlled fish oil product. In certain aspects, the biomarker promoter is selected from the group consisting of CHOP promoter, BiP promoter, ATF-4 promoter, Xbp-1 promoter or an amino acid synthetase promoter, and the like or other promoters similarly induced by inhibition of translation initiation.

In certain further exemplary embodiments of the present invention, methods are provided for the detection, using nucleic acid detection methods, such as real-time PCR of transcripts that increase in a sample as a result of omega-3 fatty acid activity. Methods are further provided for the detection of transcripts in a sample that increase as a result of omega-3 fatty acid activity through detection of activity of reporter proteins encoded by genes under the influence of promoters that are transcriptionally upregulated by omega-3 fatty acids. Methods are further provided for the detection of increased translation of transcripts that have two or more open reading frames in their 5'UTRs. Methods are still further provided for the manufacture of quality-controlled food, nutriceutical and medicinal products using the method of detecting transcripts in a sample that increase as a result of omega-3 fatty acid activity.

In certain further exemplary embodiments of the present invention, methods are provided for determining the potency of a composition having translation initiation inhibitory activity comprising the steps of contacting an eIf2α-WT cell with said composition for a time at a temperature effective to inhibit proliferation of said cells, and determining the degree of inhibition of proliferation of said cells induced by said composition, wherein the amount of said activity in said composition is proportional to the degree of inhibition of proliferation of said eIf2α-WT cells

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION OF THE INVENTION

The paradoxical observation has been made that some mRNAs are translated more efficiently when the ternary complex is scarce than when it is abundant (Aktas et al., 2004, *Journal of Nutrition* 134(9): 2487S-2491S; Halperin and Aktas, International Patent Application publication No. WO 2008/008333). These include the mRNA encoding for the transcription factor ATF-4, which transcriptionally up-regulates many of the ER stress response genes such as pro-apoptotic C/EBP-homologous protein (CHOP) or the ER chaperone binding protein (BiP) (Harding et al., 2000, *Mol. Cell* 6:1099). An isoform of the BRCA1 mRNA, designated mRNAb, also is more efficiently translated when the ternary complex is scarce. It was observed that the n-3 polyunsaturated fatty acid eicosapentaenoic acid (EPA) up-regulated CHOP (GenBank accession number S40706) and Glucose regulated protein 78 (BiP, RefSeq accession number NM_005347) in cancer cells and in tumors excised from either animal cancer models or human patients, and that it increased the translation of BRCA1 mRNAb in breast cancer cell lines and animal tumors.

Each of BRCA1 mRNA and the mRNA that encodes Activating Transcription Factor 4 (ATF-4, RefSeq accession number NM_001675) contains multiple open reading frames (ORFs) in its 5' untranslated region (5' UTR). Without intending to be bound by scientific theory, additional mRNAs that contain two or more ORFs in their respective 5' UTRs have now been identified. Such mRNAs include, without limitation, the mRNA transcripts of the genes that encode translationally controlled tumor protein (TCTP, RefSeq accession number NM_003295.2), protectin (CD59) and general control nondepressible 4 (GCN4, RefSeq accession NC_00113). According to certain exemplary embodiments, a sample of a food, nutriceutical or medicinal product may be assayed for its ability to increase the presence, level or biological activity of a protein encoded by an mRNA transcript having multiple ORFs in its 5' UTR. In particular, such a sample may be assayed for its ability to mediate an increase in the presence, level or activity of one or more of BRCA1, ATF-4, TCTP, CD59 and GCN4.

Increased transcription of certain genes also occurs in the presence of inhibitors of the ternary complex. In addition to genes that encode ATF-4, BiP and CHOP, genes that exhibit increased transcription in the presence of inhibitors of translation initiation are those that encode X-box binding protein 1(Xbp-1, RefSeq accession number NM_001079539.1) and amino acid synthetases. Such genes provide appropriate test biomarkers for translation initiation inhibitors assayed according to the invention, such as those found in fish oil. These gene transcripts can be detected, and their levels quantitated, before and after exposure of test animals, cells or cell-free systems to the test food, nutriceutical or medicinal product sample by methods known in the art, and the levels of the transcripts compared to determine the extent to which the test sample facilitated transcription of the marker gene. Alternatively, the levels of the test biomarker transcripts can be compared to those of control transcripts (e.g., of housekeeping genes) or to transcripts isolated from animals, cells or cell-free systems exposed to standards or controls of known biological activity. Similarly, the protein products of the biomarker transcripts can be detected and quantified, and their levels compared to those of untreated animals, cells or cell-free systems or to animals, cells or systems exposed to a standard or control of known biological activity.

The term "nutriceutical," as used herein, is a combination of "nutritional" and "pharmaceutical," and refers to an ingestible substance that has one or more beneficial effects on an organism such as a human. The term nutriceutical can also refer to one or more compounds which are present in an ingestible substance. Ingestible substances include, but not limited to dietary supplements, foods, beverages and the like. The terms "nutriceutical" and "nutritional supplement" may be used interchangeably. A substance (e.g., a food product, a nutriceutical product or a pharmaceutical) having beneficial biological, nutriceutical or medicinal properties refers to the ability of the substance to provide an individual one or more health benefits as described herein (e.g., in the prevention, reduction and/or cure of one or more diseases and/or disorders described herein).

Nutriceuticals of the present invention include oils derived from fish such as cold water fish, warm water fish, fresh water fish, salt water fish, brackish water fish, wild fish, farm-raised fish and the like, and preparations of fatty acids such as those containing omega-3 fatty acids.

The term "omega-3 fatty acid," as used herein, refers to polyunsaturated fatty acids such as those found in oil from oily fish such as mackerel, salmon, sardines and the like, or vegetable sources such as the seeds of chia, perilla, flax, walnut, purslane, ligonberry, seabuckthorn, hemp, and the like, and fruits from plants such as the acai palm. Omega-3 fatty acids include, but are not limited to, α-linoleic acid (ALA), eicosapentaenoic acid (EPA), docosahexaenoic acid (DHA) and the like.

Certain aspects of the present invention are directed to methods of determining the potency of a composition to inhibit upregulate or modulate translation initiation or gene transcription. The term "potency," as used herein, is intended to include, but is not limited to, the effectiveness of a compound, e.g., a nutriceutical, to inhibit, upregulate or otherwise modulate translation initiation or gene transcription. The potency of a composition can be defined as the ability of the composition to inhibit upregulate or otherwise modulate translation initiation or gene transcription relative to a standard or control.

A standard or control of the present invention is a compound or composition having a translation initiation- or transcription inhibition, upregulation or modulation activity as determined by one or more of the bioassays described herein. Standards may be obtained from a variety of sources such as the sources of omega-3 fatty acids or other agents described herein.

Standards may be synthesized in the laboratory or obtained from commercial sources. A standard may be diluted or concentrated to decrease or increase its translation inhibition, upregulation or modulation activity, respectively. Alternatively, a standard or control may be internal to the test system, e.g., a gene, gene promoter, mRNA transcript or protein (e.g., a housekeeping gene, promoter, transcript or protein) whose transcription or translation is substantially unaffected by the test substance, e.g., β-actin, ubiquitin, b-tubulin, GADPH and the like.

In certain aspects, a standard or control is an omega-3 fatty acid, such as eicosapentaenoic acid. The standard or control may be derived from fish oil (e.g., marine fish oil) or flax seed oil.

In other aspects, a standard or control is a biomarker that is substantially insensitive to the effects of the substance whose potency or biological activity is being assayed. As used in this context with respect to transcriptional regulation of a gene or gene promoter, or translational regulation of an mRNA transcript or protein, the term "substantially insensitive" means either wholly unaffected or modulated to significantly lesser extent (e.g., at least 10-fold, 100-fold, 1000-fold or greater than 1000-fold less) by the test substance than is a biomarker for activity of the test substance.

In certain aspects, a test sample is calibrated such that its active components are in the linear range and do not saturate the test system. Methods of calibrating are well known in the art and include simple dilutions, serial dilutions and the like.

The present invention provides assays in which the translation or transcription inhibition, upregulation or modulation activity of a composition is compared to a standard using one or more of the bioassays described herein. A composition may have an activity level that is 0.001%, 0.01%, 0.1%, 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 101%, 102%, 103%, 104%, 105%, 106%, 107%, 108%, 109%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, 400%, 450%, 500%, 550%, 600%, 650%, 700%, 750%, 800%, 850%, 900%, 950%, 1000%, or greater than 1000% of the activity of the standard or control.

In certain aspects, inhibition, upregulation or other modulation of activity with respect to translation initiation or gene transcription is between about 1% and 200%, between about 5% and 195%, between about 10% and 190%, between about 20% and 180%, between about 30% and 170%, between about 40% and 160%, between about 50% and 150%, between about 60% and 140%, between about 65% and 135%, between about 70% and 130%, between about 75% and 125%, between about 80% and 120%, between about 85% and 115%, between about 90% and 110%, between about 91% and 109%, between about 92% and 108%, between about 93% and 107%, between about 94% and 106%, between about 95% and 105%, between about 96% and 104%, between about 97% and 103%, between about 98% and 102%, or between about 99% and 101%, of the activity of the standard or control. In other aspects, inhibition, upregulation or other modulation of activity with respect to translation initiation or gene transcription is between about 50% and about 150% of the activity of the standard, between about 80% and about 120% of the activity of the standard, between about 90% and about 110% of the activity of the standard, or between about 95% and about 105% of the activity of the standard or control.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor or two of a given value.

In certain embodiments of the present invention, a control or standard may have zero activity. Thus, a binary result (i.e., positive or negative) may be obtained for a given activity. In such a case, if precise quantitation of activity is needed, it would be measured on an absolute scale or in comparison to a standard that has at least some activity of a known level.

A nutriceutical or composition including a nutriceutical of the present invention may be diluted or concentrated to decrease or increase its translation or transcription inhibition, upregulation or modulation activity relative to the control/standard, respectively.

The present invention also provides assays in which batch or lot homogeneity of compositions is determined by comparing the relative activity of two or more (e.g., 10, 100, 1000, 10,000 1,000,000 or more) compositions using one or more of the bioassays described herein. As used herein, the terms "batch homogeneity" or "lot homogeneity" are intended to refer, but are not limited to, the relative translation initiation inhibition upregulation or modulation activity, or transcriptional upregulation activity, of two or more compositions in a batch or lot. As used herein, the terms "batch" or "lot" refer, but are not limited to, a group of two or more compositions. A batch or lot includes compositions prepared together or compositions from two or more sources (e.g., geographical, plant, animal, commercial, and/or synthetic sources). As used herein, the term "batch" or "lot" also may refer to a single pool of a composition, from which units of products or test samples are to be drawn or produced, or which will be otherwise further divided or fractionated.

In at least certain examples, the nutriceuticals disclosed herein can be used in the treatment of disorders associated with aberrant cellular proliferation such as cellular proliferative disorders, (e.g., cancer). Treatment of cellular proliferative disorders is intended to include inhibition of proliferation including rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition, 1995). The terms "neoplasm" and "tumor" refer to an abnormal tissue that grows by cellular proliferation more rapidly than normal and continues to grow after the stimuli that initiated proliferation is removed (see, for example, PDR Medical Dictionary 1st edition, 1995). Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include the prevention of the induction, onset, establishment or growth of neoplasms in a subject or a reduction in the growth of pre-existing neoplasms in a subject. The language also can describe inhibition of the invasion of neoplastic cells into neighboring tissues or the metastasis of a neoplasm from one site to another. Examples of the types of neoplasms intended to be encompassed by the present invention include but are not limited to those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Cellular proliferative disorders can further include disorders associated with hyperproliferation of vascular smooth muscle cells such as proliferative cardiovascular disorders, e.g., atherosclerosis and restenosis. Cellular proliferation disorders can also include disorders such as proliferative skin disorders, e.g., X-linked ichthyosis, psoriasis, atopic dermatitis, allergic contact dermatitis, epidermolytic hyperkeratosis, and seborrheic dermatitis. Cellular proliferative disorders can further include disorders such as autosomal dominant polycystic kidney disease (ADPKD), mastocystosis, and cellular proliferation disorders caused by infectious agents such as viruses.

In at least certain examples, the nutriceuticals assayed and/or produced according to the methods disclosed herein can be used in the treatment of disorders associated with energy balance, such as metabolic disorders including, but not limited to, diabetes, obesity, glycogen storage diseases, lipid storage disorders, mitochondrial diseases and the like (see also the Worldwide Website: emedicine.com/ped/GE-NETICS_AND_METABOLIC_DISEASE.htm). In certain aspects, the nutriceuticals assayed and/or produced according to the methods disclosed herein modulate weight gain by interacting with the 5' UTR of the leptin receptor.

Detection methods described herein can be used to detect one or more DNA sequences, RNA sequences, proteins or polypeptides of interest in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a protein and/or polypeptide include introducing into a subject a labeled antibody directed against the protein and/or polypeptide. For example, the antibody can be labeled with a radioactive marker whose presence and location in a subject can be detected by standard imaging techniques.

A general principle of detection and/or quantification involves preparing a sample or reaction mixture that may contain one or more DNA sequences, RNA sequences, proteins or polypeptides of interest and a probe under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the DNA sequence, RNA sequence, protein or polypeptide of interest or a probe onto a solid phase support, also referred to as a substrate, and detecting target DNA sequence, RNA sequence, protein or polypeptide of interest/probe complexes anchored on the solid phase at the end of the reaction. In one embodiment of such a method, a sample which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of DNA sequence, RNA sequence, protein or polypeptide of interest/probe complexes anchored to the solid phase can be accomplished in a number of methods outlined herein.

In certain exemplary embodiments, the probe, when it is the unanchored assay component, can be labeled for the purpose of detection and readout of the assay, either directly or indirectly, with detectable markers which are well-known to one skilled in the art. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, $^{3}H$ or $^{32}P$. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology*, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander et al. (1991) *Anal. Chem.* 63:2338 2345 and Szabo et al. (1995) *Curr. Opin. Struct. Biol.* 5:699 705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous detection and/or quantification assays can be conducted with one or more DNA sequences, RNA sequences, proteins or polypeptides of interest and probe as solutes in a liquid phase. In such an assay, the complexed DNA sequence, RNA sequence, protein or polypeptide of interest and probe are separated from uncomplexed components by any of a number of standard techniques, including but not limited to: differential centrifugation, chromatography, electrophoresis and immunoprecipitation. In differential centrifugation, DNA sequence, RNA sequence, protein or polypeptide of interest/probe complexes may be separated from uncomplexed assay components through a series of centrifugal steps, due to the different sedimentation equilibria of complexes based on their different sizes and densities (see, for example, Rivas and Minton (1993) *Trends Biochem Sci.* 18:284). Standard chromatographic techniques may also be utilized to separate complexed molecules from uncomplexed ones. For example, gel filtration chromatography separates molecules based on size, and through the utilization of an appropriate gel filtration resin in a column format; for example, the relatively larger complex may be separated from the relatively smaller uncomplexed components. Similarly, the relatively different charge properties of the DNA sequence, RNA sequence, protein or polypeptide of interest/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard (1998) *J. Mol. Recognit.* 11:141; Hage and Tweed (1997) *J. Chromatogr. B. Biomed. Sci. Appl.* 12:499). Gel electrophoresis may also be employed to separate complexed assay components from unbound components (see, e.g., Ausubel et al., ed., *Current Protocols in Molecular Biology*, John Wiley & Sons, New York, 1987 1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In certain exemplary embodiments, the level of an mRNA sequence of interest can be determined either by in situ and/or by in vitro formats in a biological sample using methods known in the art. Many expression detection methods use isolated RNA. For in vitro methods, any RNA isolation technique that does not select against the isolation of mRNA can be utilized for the purification of RNA from blood cells (see, e.g., Ausubel et al, ed., *Current Protocols in Molecular Biology*, John Wiley & Sons, New York 1987 1999). Additionally, large numbers of cells and/or samples can readily be processed using techniques well known to those of skill in the art, such as, for example, the single-step RNA isolation process of Chomczynski (1989, U.S. Pat. No. 4,843,155).

Isolated mRNA can be used in hybridization or amplification assays that include, but are not limited to, Southern or Northern analyses, polymerase chain reaction analyses and probe arrays. In certain exemplary embodiments, a diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker of the present invention. Other suitable probes for use in the diagnostic assays of the invention are described herein.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in U.S. Pat. Nos. 4,683,195 and 4,683,202), COLD-PCR (Li et al. (2008) *Nat. Med.* 14:579), ligase chain reaction (Barany, 1991, *Proc. Natl. Acad. Sci. USA*, 88:189), self sustained sequence replication (Guatelli et al., 1990, *Proc. Natl. Acad. Sci. USA* 87:1874), transcriptional amplification system (Kwoh et al. (1989) *Proc. Natl. Acad. Sci. USA* 86:1173), Q-Beta Replicase (Lizardi et al. (1988) *Bio/Technology* 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the sample (e.g., a bodily fluid (e.g., blood cells)) prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the DNA sequence, RNA sequence, protein or polypeptide of interest, determinations may be based on the normalized expression level of the DNA sequence, RNA sequence, protein or polypeptide of interest. Expression levels are normalized by correcting the absolute expression level of a DNA sequence, RNA sequence, protein or polypeptide of interest by comparing its expression to the expression of a gene that is not a marker, e.g., a standard or control. This normalization allows the comparison of the expression level in a sample from one source to a sample from another source.

In another exemplary embodiment, a protein or polypeptide is detected. In certain exemplary embodiments, an agent for detecting a polypeptide of the invention is an antibody capable of binding to a polypeptide corresponding to a marker of the invention, such as an antibody with a detectable label. Antibodies can be polyclonal, or more preferably, monoclonal. An intact antibody, or a fragment thereof (e.g., Fab or F(ab')$_2$) can be used. The term "labeled," with respect to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Polyclonal antibodies can be prepared by immunizing a suitable subject with a protein or polypeptide of choice. The protein of choice titer in the immunized subject can be monitored over time by standard techniques, such as with an enzyme linked immunosorbent assay (ELISA) using immobilized protein. If desired, the antibody molecules directed against the protein of choice can be isolated from the mammal (e.g., from the blood) and further purified by well known techniques, such as protein A chromatography to obtain the IgG fraction. At an appropriate time after immunization, e.g., when the anti-protein of choice antibody titers are highest, antibody-producing cells can be obtained from the subject and used to prepare monoclonal antibodies by standard techniques, such as the hybridoma technique originally described by Kohler and Milstein (1975) *Nature* 256: 495-497) (see also, Brown et al. (1981) *J. Immunol.* 127: 539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with a protein of choice as described above, and the culture supernatants of the resulting hybridoma cells are screened to identify a hybridoma producing a monoclonal antibody that binds the protein of choice.

A variety of formats can be employed to determine whether a sample contains a protein that binds to a given antibody. Examples of such formats include, but are not limited to, enzyme immunoassay (ETA), radioimmunoassay (RIA), Western blot analysis, enzyme linked immunoabsorbant assay (ELISA) and the like. A skilled artisan can readily adapt known protein/antibody detection methods for use in determining whether cells (e.g., bodily fluid cells such as blood cells) express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well known supports or carriers include glass, polystyrene, polypropylene, polyethylene, dextran, nylon, amylases, natural and modified celluloses, polyacrylamides, gabbros, magnetite and the like.

One skilled in the art will know many other suitable carriers for binding antibody or antigen, and will be able to adapt such support for use with the present invention. For example, protein isolated from cells (e.g., bodily fluid cells such as blood cells) can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In certain exemplary embodiments, assays of the invention may be performed in animal models (including, but not limited to horses, cows, sheep, pigs, goats, rabbits, guinea pigs, rats, mice, gerbils, non-human primates and the like), cells (e.g., cells from microorganisms (e.g., bacterial cells, viral cells, yeast cells and the like)) or cell-free systems (e.g., in vitro transcription assays, in vitro translation assays, cell lysate assays, fractionated cell lysate assays and the like).

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables, and accompanying claims.

EXAMPLE 1

Preparation of Samples for Bioassay

The active ingredient of many nutriceuticals such as fish oil is released upon digestion. It is therefore necessary to mimic this digestion in the test tube in order to test the in vitro activity of fish oil (such as cell culture). There are several ways of achieving this, one such method is described below as a non-limiting example.

Fish Oil Hydrolysis

Fish Oil (10 g.~12 mmol) and NaOH (2.16 g. 54 mmol) were mixed in water (50 ml), absolute ethanol (70 ml), and toluene (10 ml). The mixture was magnetically stirred and refluxed under $N_2$ for 1.5 h. The reaction mixture was cooled to room temperature, treated with 1N HCl (81 ml) and extracted with n-hexane (100 ml). The organic phase was washed with a mixture of ethanol/water (1:1, v/v) until reaching an aqueous phase of pH 5. The separated organic phase was dried over anhydrous $Na_2SO_4$, filtered and the solvent removed under vacuum at room temperature. The residue obtained is the fish oil hydrolysate that is subjected to quantitative composition analysis and biological activity characterization.

EXAMPLE 2

Detection of Biomarker mRNA by Real Time PCR

Real-time PCR is a quantitative method for detecting changes in the levels of specific RNAs; therefore, real-time PCR for pro-apoptotic or tumor suppressor genes transcriptionally upregulated in the presence of inhibitors of the ternary complex provides a rapid and accurate quantitative assay for evaluating the availability of the ternary complex, and is an effective surrogate assay for detection of the phosphorylation of eIf2α induced by omega-3 fatty acids. It has been determined that this new assay also has shown remarkable correlation with those obtained through use of an existing ATF-4 cell-based assay that is highly dependent on availability of the ternary complex. It is, therefore, an improved method for quality-control and assurance of food, nutriceutical and medicinal products with respect to the activity of omega-3 fatty acids and other beneficial compounds that influence availability of the ternary complex to initiate mRNA translation.

Standard Real-Time PCR Assay

1. Plate cells of either human mouse or rat origin such as, e.g., rat hepatocytes, mouse or human fibroblast grown in standard culture media such as, e.g., DMEM or RPMI 1640 with 5-10% fetal bovine or bovine calf serum (either three wells in 6-well or 100 mm plate, or other container) for each condition;
2. Treat with compound to be evaluated or with control/standard vehicle;
3. Harvest cells after six hours;
4. Isolate RNA;
5. Reverse transcribe RNA;
6. Amplify reverse transcripts of biomarker mRNA (e.g., that which encodes CHOP, BiP, ATF-4, Xbp-1 or an amino acid synthetase) and those of 18S RNA (internal standard);
7. Quantify amount of biomarker reverse transcript after normalization against 18S reverse transcript; and
8. Compare amounts of biomarker reverse transcript across differently-treated samples (e.g., treated with test compounds or vehicle).

In Cell, Real Time PCR Assay

1. Plate cells (e.g., in 96-well plates or other multichamber format);
2. Treat with different doses of compounds or vehicle;
3. Lyse cells after 6 hours;
4. Reverse transcribe in the same wells;
5. Amplify reverse transcript of biomarker mRNA (e.g., that which encodes CHOP, BiP, ATF-4, Xbp-1 or an amino acid synthetase) and that of 18S RNA in the same well;
6. Quantify amount of biomarker reverse transcript after normalization against 18S reverse transcript; and
7. Compare amounts of biomarker reverse transcript across differently-treated samples (e.g., treated with test compounds or vehicle).

Figure 1:
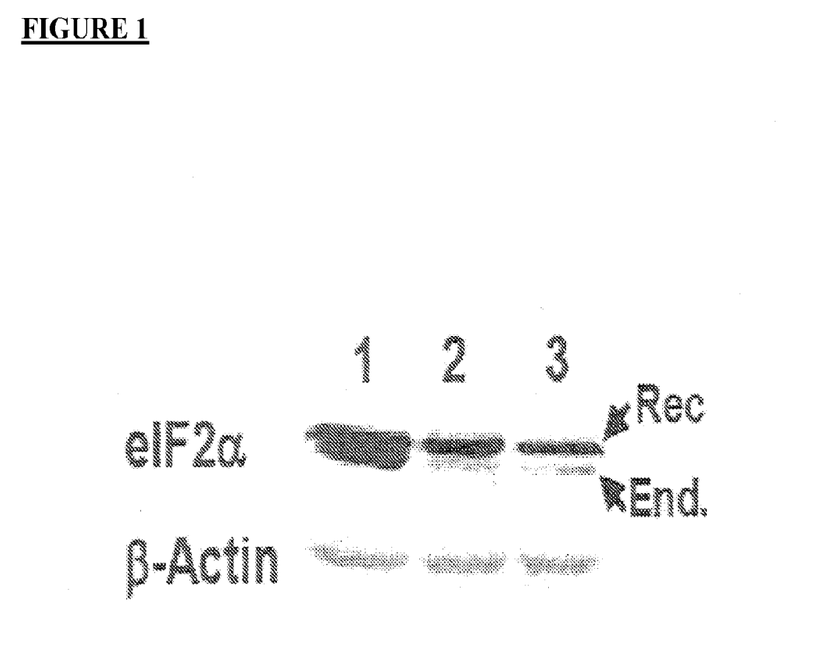
FIG. 1 is a Western blot using anti-total eIf2α or β-actin antibodies Lane 1 is cells transduced with the pLVTHM vector without shRNA, lanes 2 and 3 are cells transduced with the pLVTHM vector containing eIf2α-WT and eIf2α-S51A ORF and shRNA #1098 cassettes.

Results obtained when a CHOP-encoding mRNA transcript was amplified are shown in FIG. 1, in comparison to results obtained in the existing ATF-4 assay.

EXAMPLE 3

Detection of Transcriptional Activity of Biomarker Genes via Reporter Gene Assay Another means by which to assay the presence and activity of omega-3 fatty acids in food, nutriceutical and medicinal compositions is to measure upregulation of marker gene transcriptional activity using reporter gene constructs. According to this method, each such construct contains a nucleic acid sequence that encodes a reporter protein (e.g., luciferase, Green Fluorescent Protein, Red, far Red, dsRed, dsRed2, orange, yellow, cyan, beta galactosidase, horseradish peroxidase, aquaporins, chloramphenicol acetyl transferase, or other protein that generates a detectable signal or has an enzymatic or other activity that is susceptible to detection by methods known to those of skill in the art). Operably linked to the reporter protein coding sequence of the construct is a naturally-occurring or synthetic promoter region that is transcriptionally upregulated in the presence of omega-3 fatty acids or other suitable inhibitors of mRNA translation initiation, e.g., ternary complex inhibitors. Suitable promoters include, in non-limiting fashion, those of the genes that encode biomarkers such as CHOP, BiP, ATF-4, Xbp-1 or amino acid synthetases. Under conditions that permit nucleic acid transcription and mRNA translation to occur, the system is contacted or treated with a test sample. Suitable negative controls include, but are not limited to, a parallel test system not so contacted or treated, or one that is contacted or treated with an appropriate standard sample. In both the test and control systems, reporter protein function is detected and quantified by methods well known in the art, and the levels of reporter function in the test and standard systems are compared to determine the potency of omega-3 fatty acids present in the test sample. In such an assay, the signal obtained using an ATF-4 promoter construct or CHOP promoter construct that also includes the native ATF-4 5'UTR is amplified to a greater degree than would those resulting from use of the other promoters, as ATF-4 is both transcriptionally and translationally upregulated in the presence of omega-3 fatty acids. Reporter constructs may be designed with this in mind, so as to keep signal levels in the linear range for the level of reporter activity that is anticipated to result from exposure to test samples, depending on their estimated potency prior to assay, e.g., based on results obtained with samples or comparable origin, processing or the like.

Certain reporter constructs of the present invention also combine high efficiency transcription promoters and high efficiency translation 5'UTRs, such as with the CHOP promoter and ATF-4 5'UTR, to provide signal amplification that is preferably geometric thereby providing an advantageous signal-to-noise ratio compared to reporter constructs including only one of the two elements. Such a reporter construct is particularly useful in assays where high sensitivity is desired such as when comparing dilute or weakly-positive samples commonly encountered during early stages of processing or when detecting a rare activity. Promoters and 5'UTRs can be combined into a single reporter construct using methods known to those of skill in the art and as described herein. Useful promoters include, in non-limiting fashion, those of the genes that encode biomarkers such as CHOP, BiP, ATF-4, Xbp-1 or amino acid synthetases and the like and others known in the art and described herein. Useful 5'UTRs include ATF-4, BRCA1 mRNAb, CD59, TCTP and GCN4 and the like and others known in the art and described herein. A useful reporter construct including both elements are particularly advantageous when the selected elements, i.e. 5'UTR and promoter pairings, respond to the same or similar agent or signal.

EXAMPLE 4

Detection of Increased Translation of Biomarker Proteins

To determine the potency of omega-3 fatty acids or other beneficial agents in food, nutriceutical or medicinal products, mRNA transcripts in which 5'UTR sequences containing two or more ORFs are operably linked to sequences that encode reporter proteins are exposed to conditions under which protein translation is permitted to occur, e.g., an animal, cell or cell-free translation system, such as a rabbit reticulocyte lysate or other in vitro system containing the cellular components necessary to effect translation of mRNA to protein. The transcripts may be produced within the system (e.g., expressed in an animal, cell or other mixture that contains the reporter construct and an appropriate nucleic acid polymerase, e.g., an RNA polymerase), or may be exogenously produced and added to the system. The system optionally may contain an internal or other control reporter mRNA whose translational efficiency is not affected by the presence of omega-3 fatty acids or other beneficial agents that the assay is intended to detect, thereby allowing for levels of test and control translational activity to be normalized against the relative amounts of test and control transcripts available to be translated. Alternatively, reporter mRNA levels may be normalized between various test samples and levels of reporter function compared.

Appropriate 5'UTRs for test transcripts include, in non-limiting fashion, those of the genes or mRNA transcripts that encode biomarker proteins such as BRCA1, ATF-4, TCTP, CD59 or GCN4. Appropriate 5'UTRs for control transcripts may be drawn from genes or mRNA transcripts that encode housekeeping proteins and/or that have one or fewer (i.e., zero) ORFs in their respective 5'UTRs.

The systems described above are treated or contacted with a sample of a food, nutriceutical or medicinal composition, and the amounts of test and control reporter protein function (e.g., within a test sample; between a test sample and an untreated sample; between a test sample and a sample treated with a standard for potency of an omega-3 fatty acid or other beneficial agent), detected and quantified by methods well known in the art, wherein elevated levels of reporter function correlate positively with translational activity of the test reporter mRNAs and, consequently, potency of an omega-3 fatty acid or other beneficial agent contained in the test sample.

EXAMPLE 5

Manufacture of Quality-Controlled Nutriceutical and Other Products from Fish Oil As mentioned above, fish oil is a significant source of omega-3 fatty acids; however, supplies of fish oil differ greatly from one another in content and bioactivity of these beneficial compounds. The invention provides methods for the manufacture of fish-oil-derived products that possess known, uniform bioactivity of omega-3 fatty acids.

Fish are caught and, while live or fresh-killed, pressed under food-grade manufacturing conditions to effect extraction of oil from the flesh. Heavy metals and other environmental contaminants are removed by filtration, chelation and/or other methods known to those of skill in the relevant art. Optionally, fish oil then may be further processed, for example, to improve taste, aroma and/or appearance, to add other beneficial agents (including, in non-limiting fashion, phytosterols or other beneficial compounds) or to concentrate omega-3 fatty acids and/or other beneficial agents. Optionally, unprocessed, partially-processed (e.g., detoxified), fractionated or otherwise processed fish oil may be packaged, for example, in bottles or other non-consumable containers, or in consumable containers, such as food- or pharmaceutical grade capsules, e.g., gel capsules or caplets. Optionally, omega-3 fatty acids and/or other beneficial agents contained in fish oil may be enriched, partially purified or even fully purified, i.e., isolated.

At one or more of the aforementioned stages of manufacture, the ability of the fish oil, intermediate product or finished product to effect increased transcription of one or more of the genes that encode biomarkers such as ATF-4, CHOP, BiP, Xbp-1 or amino acid synthetases, or, alternatively, increased translation of mRNAs containing in their 5'UTRs two or more ORFs, including, in non-limiting fashion, 5'UTRs from mRNAs that encode biomarkers such as BRCA1, ATF-4, TCTP, CD59 or GCN4, is assayed using the methods described in the preceding Examples herein. Assay results obtained during early stages of manufacture may enable adjustments to be made in concentration of omega-3 fatty acids during further production steps, or may otherwise guide assembly, mixture or formulation of product components to result in a food, nutriceutical or medicinal product of known potency with regard to omega-3 fatty acid bioactivity. Optionally, samples of the finished product (e.g., an aliquot of a liquid or powder, or a single caplet, each representative of the batch or lot from which is has been drawn or selected) may be assayed prior to distribution, thereby enabling label or other marketing claims to be made with respect to the level of a beneficial biological, nutriceutical or medicinal property possessed by the product, e.g., with respect to the inhibition of translation initiation, or therapeutic or preventive properties associated with the inhibition, upregulation or other modulation of biomarker gene transcription or mRNA translation.

EXAMPLE 6

Development or Robust, Sensitive Cell-Based Assays that Allow for the Quantification of the Anti-Cancer Biological Activity of Nutriceutical-Grade Fish Oil (NFO) Preparations/Batches.

Study Design:

Generation of Transgenic Human Prostate Cancer Cell Lines Expressing Mutant (eIf2α-S51A EPA-resistant) or Wild Type (eIf2α-WT$_2$ EPA-sensitive) eIf2α.

Objective: To determine the cause-effect relationship between phosphorylation of eIf2α and anti-cancer activity of n-3 PUFAs in human prostate cancer cell lines. Cells were engineered that express non-phosphorylatable mutant (eIf2α-S51A) or recombinant wild type eIf2α (eIf2α-WT) and red fluorescent or green fluorescent proteins, respectively in the absence of endogenous eIf2α. To differentiate recombinant eIf2α proteins from endogenous eIf2α proteins, recombinant eIf2α was N-terminally tagged with a hemagglutinin (HA) tag to ensure co-expression of recombinant eIf2α (S51A mutant or WT) and the fluorescent protein. A recently disclosed technique was used wherein two proteins can be translated at a 1:1 ratio. This is accomplished by cloning their coding sequences as a single monocistronic mRNA provided that the amino acid sequences of these two proteins are separated by a protease 2A cut site. In other words, a pro-protein translated from a single Open reading frame (ORF) is cut by the protease 2A to generate HA-tagged eIf2α (WT or S51A) and RFP or GFP proteins.

In the specific construct herein, cleavage by protease 2A created HA-tagged native eIf2α and a fusion of fluorescent protein with the protease 2A recognition sequence. In order to silence endogenous eIf2α with shRNA without affecting recombinant eIf2α (WT or S51A), all 5' and 3'UTR elements of the eIf2α gene were excised from the plasmid.

Experimental Design:

The design required replacement of endogenous eIF2a with recombinant eIF2α (WT or S51A) protein to be temporally regulated. To accomplish this a pLVTHM lentiviral vector was utilized. This vector contains a human elongation factor 1 promoter-controlled cassette for expression of an ORF in mammalian cells and a viral LTR/SIN-controlled cassette for shRNA mediated gene silencing. eIF2α-WT in tandem with GFP and eIF2α-51A in tandem with RFP coding sequences were used. The protease 2A cut site was inserted between eIF2a (WT or S51A) and fluorescent proteins. RFP and GFP used to tag the cells. These two reporters were selected because they can easily be distinguished under the microscope using appropriate filters in vitro and in vivo. For optimal translation, the ORFs were preceded by a perfect Kozak consensus sequence (GCCAC-CATGG) (SEQ ID NO:1). To identify the best shRNA sequence that targets endogenous but not recombinant eIF2α, several candidate lentiviral shRNAs targeting 5' or 3'UTRs of endogenous eIF2α were screened using Western Blot analysis to evaluate each shRNA. Through these studies it was demonstrated that one of the shRNA sequences, shRNA #1098, caused near-total abolishment of the endogenous eIF2α expression. This shRNA was cloned into the shRNA expression cassette of the pLVTHM vector.

Generation of Transgenic Human Prostate Cancer Cell Lines that Replace Expression of Endogenous eIf2α with Recombinant Protein (eIf2α-S51A or eIf2α-WT).

Human PC-3 prostate cancer cell lines were transduced with the pLVTHM vector coding for eIf2α-S51A or eIf2α-WT and RFP and cells expressing similar levels of RFP by FACS sorting were selected. The cells were expanded and characterized for expression of transgenic eIf2α (WT or S51A) relative to endogenous eIf2α using high resolution SDS-PAGE electrophoresis and Western BFlot analysis with goat anti-eIf2α antibodies that recognizes both endogenous and recombinant eIf2α and Alexa-680 conjugated anti-goat antibodies. Prostate cancer cells transduced with the above-described lentiviral vector express two eIf2α isoforms, a faster migrating protein corresponding to the endogenous eIf2α and a slower migrating protein corresponding to the tagged recombinant eIf2α (the HA tag adds about 1.5 kd). That this slower migrating protein was indeed transgenic eIf2α was confirmed by blotting the same gels with monoclonal anti-HA antibodies and Alexa-800 conjugated anti-mouse antibodies (not shown). Because the anti-eIf2α antibody can recognize both endogenous and recombinant eIf2α, presumably with the same affinity, relative expression of endogenous and recombinant eIf2α can be quantified by Western blot analysis with a single anti-eIf2α antibody.

PC-3 human prostate cancer cell lines were transduced with the pLVTHM vector coding for eIf2α-S51A/RFP or eIf2α-WT/RFP and shRNA#1098 and cell lysates were blotted with anti-total eIf2α or β-actin antibodies. In FIG. 1, Lane 1 is cells transduced with pLVTHM vector without shRNA, lanes 2 and 3 are cells transduced with pLVTHM vector containing eIf2α-WT or eIf2α-S51A ORF and shRNA #1098 cassettes. Cells transduced with the pLVTHM vector without the shRNA insert expressed about as much recombinant protein as endogenous eIf2α.

Figure 2:
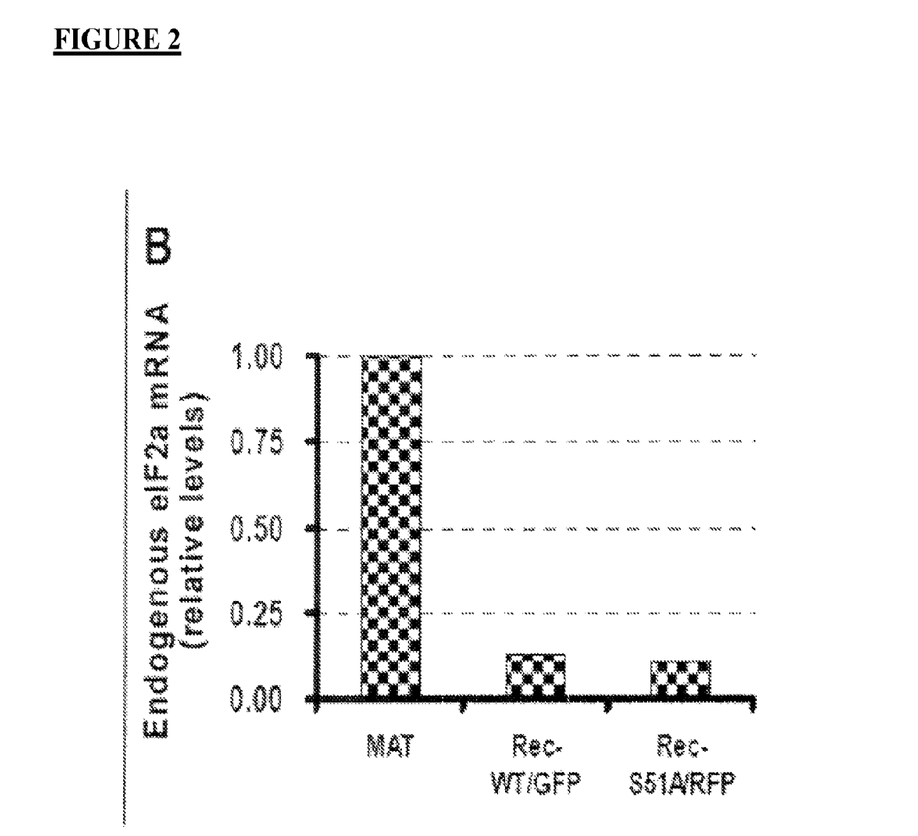
FIG. 2 is a graph showing endogenous eIf2α mRNA levels determined by real time PCR in maternal (Mat) and recombinant (Rec) eIf2α-WT (GFP) and eIf2α-S51A/RFP or eIf2α-WT/RFP cells. Lane 1 is cells transduced with the pLVTHM without shRNA, lanes 2 and 3 are cells transduced with the pLVTHM vector containing eIf2α-WT and eIf2α-S51A ORF and shRNA #1098 cassettes.

Expression of endogenous eIf2α protein was dramatically reduced in cells transduced with the pLVTHM vector containing the shRNA #1098. This viral vector consistently reduced endogenous eIf2α mRNA expression by ~85% (FIG. 2.). These data indicate that endogenous eIf2α was successfully replaced with recombinant eIf2α (either WT or S51A mutant) while maintaining overall eIf2α levels as close to those in parental cells as possible.

Figure 3:
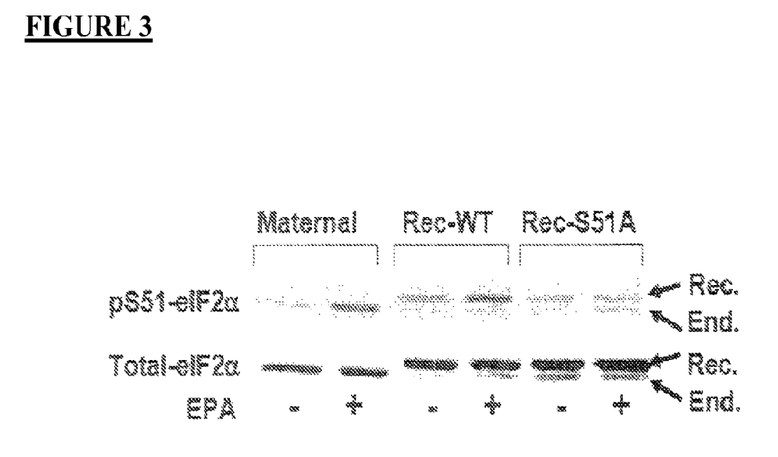
FIG. 3 is a Western blot. Cells in FIG. 2 were treated with vehicle or EPA and lysates were probed with antibodies to $pS_{51}$-eIf2α (top) or total eIf2α (bottom). Rec=recombinant, End=endogenous eIf2α.

The transgenic cell lines were characterized for their response to EPA-induced eIf2α phosphorylation. EPA caused phosphorylation of both the endogenous eIf2α and recombinant eIf2α-WT but not recombinant eIf2α-S51A (see for example FIG. 3 for effects of EPA). Consequently, EPA caused a significant phosphorylation of eIf2α in maternal or recombinant eIf2α-WT expressing cells but not in recombinant eIf2α-S51A expressing cells.

Figure 4:
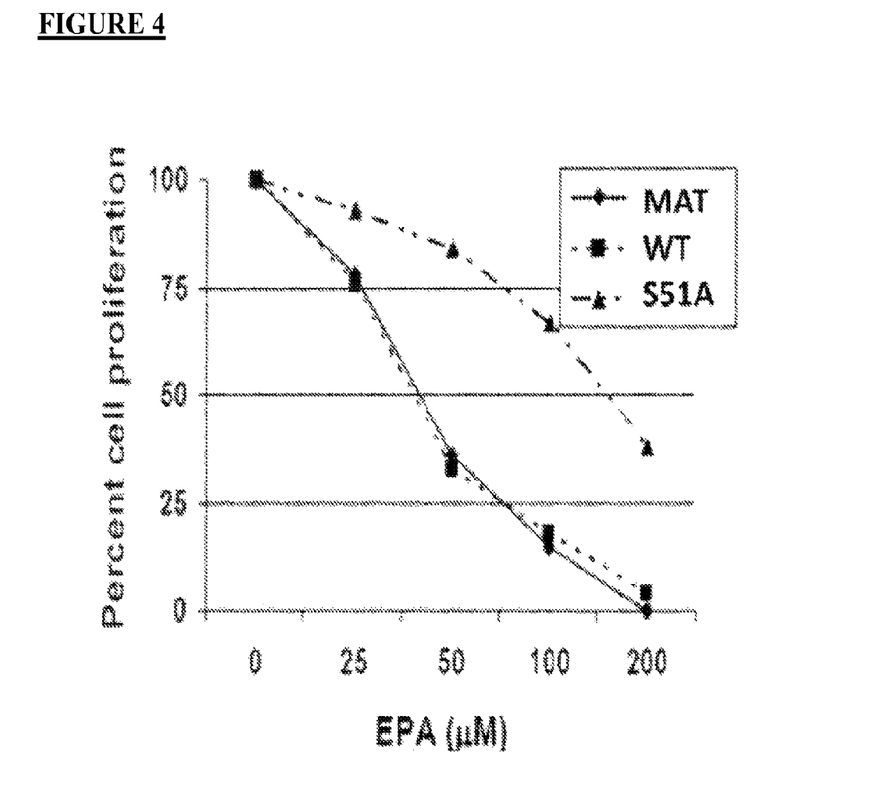
FIG. 4 is a graph showing eIf2α-S51A expressing cells are resistant to inhibition of cell proliferation induced by EPA whereas proliferation of maternal PC-3 cells (MAT) or PC-3 cells transduced with recombinant eIf2α RFP and shRNA are sensitive to inhibition of cell proliferation induced by EPA in a dose-dependent manner.

Maternal PC-3 cells (MAT) or PC-3 cells transduced with recombinant eIf2α RFP and shRNA (#1 at position 1098 in 3'UTR of endogenous but not recombinant mRNA) expression vector targeting the expression of endogenous eIf2α were cultured in the presence of increasing concentrations of EPA. Net cell proliferation was quantified by SRB assay after five days of incubation and expressed as percent of control cells treated with vehicle. As shown in FIG. 4, PC-3 cells expressing recombinant eIf2α-WT were sensitive to inhibition of cell proliferation by EPA in a dose dependent manner while those expressing recombinant eIf2α-S51A were resistant.

In conclusion a cell-based assay has been described herein that utilizes molecularly engineered cells to measure the translation-initiation inhibitory specific activity of omega-3 concentrates or other nutriceuticals that exert their biological activity by eIf2α-mediated inhibition of translation initiation. The assays are accurate and sensitive because they measure activity in a sample in the absence of endogenous eIf2α activity.

These findings demonstrate that the transgenic human cancer cells disclosed herein are excellent tools for assessing the biological activity of the nutriceutical preparations of the present invention and omega-3 concentrates that induce phosphorylation of eIf2α and for quality control of such preparations.

PC-3 eIf2α-WT (strain 351) and PC-3 eIf2α-S51A (strain 411) cell cultures were deposited with the American Type Culture Collection (ATCC Manassas, Va.) on Jun. 22, 2012 and received ATCC accession Nos. PTA-13010 and PTA-13011, respectively.

The cell-based assay of the present invention is performed as follows:

Cells: Between about 1000 and about 2000 eIf2α-S51A or eIf2α-WT cells are cultured In each well of a 96 well plate at a temperature of about 37° C. for about one day Media: Complete (5% fetal calf serum added) tissue culture media RPMI-1640 (Invitrogen, CA)

Materials:
96-well tissue culture plates
Sulforhodamine B dye (SRB, 0.57% v/w, Sigma, IL)
Tricarbocilicacetic acid (TCA, 10%, Sigma IL)
Acetic Acid glacial (1%, Sigma, IL)
10 mM Tris base (Sigma, IL)
100 mM compound stock
Prepare/plate the cells
Grow cancer cells to 80% confluency
Trypsinize per standard protocol
Neutralize trypsin, dissociate cells and count.
Plate 1000 cells in 100 μl media per each well of 96-well plate
Leave wells at the edges empty
Need 1 plate for 4 compounds Plate cells in another plate (12 wells per cell line), label this as "day 0" plate
Add compounds (next day)
Add 50 μl 10% TCA to day 0 plate, store at 4° C.
Prepare 40, 12, 3.6, 1.62, and 0 (solvent) μM compound in culture medium
Maintain solvent (DMSO) concentration the same across dilutions
Add 100 μl of each compound dilution to three wells of each plate for a cell line
Final compound concentrations are 20, 6, 1.8, 0.54, and 0 μM
Return cells to incubator
Five days after compound additions add 100 μl 10% TCA
Incubate at 4° C. minimum of 1 h.
SRB staining
Follow the protocol of Vichai and Kirtikara (Nature Methods 2006, vol 1:1112-1115)
a) Stain the cells
Remove cells from cold room
Decant the content
Wash four times with single distilled $H_2O$
Remove excess 0
Dry the plates (blow dry or air dry)
Add 100 μl 0.057% SRB solution to each well
Incubate RT 30 min
Decant the dye
Wash with 1% acetic acid four times
Air dry plates
b) Measure the OD
Add 200 μl 10 mM TRIS-base (~pH 10.5) to each well
Shake plate for 5-10 min
Read OD at 510 nM in microplate reader Calculate percent cell growth inhibition as % of control cell growth=((Mean OD sample-Mean OD day 0)/(mean OD vehicle-Mean OD day0))× 100% growth inhibition=100-% of control cell growth The assay uses a standard for comparative purposes, which is a previously assayed nutriceutical or a predetermined amount of EPA. eIf2α-S51A cells are prepared and used as a negative control for substances which inhibit cell proliferation independently of eIf2α. FIG. 4 is an example of a standard curve. The standard curve shows that the amount of inhibition of proliferation is proportional to the amount of nutriceutical of the present invention or EPA. The standard is performed with every assay to determine the amount of activity in a sample because the degree of inhibition of proliferation is proportional to the amount of nutriceutical of the present invention.

What is claimed is:

1. A method for determining the translation initiation inhibitory potency of a composition having an unknown level of translation initiation inhibitory activity which comprises: contacting an ATCC accession No. PTA-13010 cell with said composition for a time and at a temperature effective to inhibit proliferation of said cell,
   contacting an ATCC accession No. PTA-13011 cell with said composition for a time and at a temperature effective to inhibit proliferation of said cell,
   measuring the level of inhibition of proliferation of said ATCC accession No. PTA-13010 cell and said ATCC accession No. PTA-13011 cell induced by said composition,
   wherein the amount of said translation initiation inhibitory activity in said composition is proportional to the level of inhibition of proliferation of ATCC accession No. PTA-13010 cell, and,
   comparing the level of inhibition of proliferation induced by said composition with the level of inhibition of proliferation induced by a standard having a known amount of said activity, and,
   identifying the composition as not having translation initiation inhibitory activity if said composition inhibits the proliferation of said ATCC accession No. PTA-13011 cell.

2. The method of claim 1 wherein said composition is a nutraceutical.

3. The method of claim 1 wherein said composition is an omega-3 concentrate.

4. The method of claim 1 wherein said standard is a composition comprising a known amount of said translation initiation inhibitory activity.

5. The method of claim 4 which comprises determining the amount of translation-initiation inhibitory activity of said composition by comparing the amount of said activity in said composition with the amount of translation initiation inhibitory activity in said standard.

6. The method of claim 5 wherein said activity in said composition is expressed as a percent of the activity in said standard.

7. The method of claim 5 wherein said standard is a known amount of eicosapentaenoic acid (EPA).

8. The method of claim 1 wherein said composition is hydrolyzed before said contacting step.

9. A method for determining the amount of translation initiation inhibitory activity in a sample comprising the steps of:
   contacting an ATCC accession No. PTA-13010 cell with said sample,
   incubating said contacted ATCC accession No. PTA-13010 cell and said sample for a time and at a temperature effective to inhibit proliferation of said ATCC accession No. PTA-13010 cell, and
   measuring the level of inhibition of cell proliferation of said ATCC accession No. PTA-13010 cell induced by said sample,
   wherein said level of inhibition of cell proliferation of said ATCC accession No. PTA-13010 cell induced by said sample is proportional to the amount of said translation initiation inhibitory activity in said sample.

10. The method of claim 9 wherein the level of inhibition of cell proliferation is expressed as a percent of the proliferation of an untreated ATCC accession No. PTA-13010 cell.

11. The method of claim 10 which comprises comparing the level of inhibition of proliferation induced by said sample to the level of inhibition of cell proliferation induced by a standard having a known amount of said activity.

12. The method of claim 10 which comprises hydrolyzing said sample before determining said inhibitory activity.

13. The method of claim 10 wherein said standard is a previously assayed sample containing a known level of said activity.

14. The method of claim 13 wherein said standard is a known amount of EPA.

15. The method of claim 9 wherein said sample is an omega-3 concentrate.

16. The method of claim 9 wherein said sample comprises a fish oil extract.

17. A human prostate cancer cell line PC-3 eIF2α-WT having ATCC accession No. PTA-13010.

18. A human prostate cancer cell line PC-3 eIF2α-S51A having ATCC accession No. PTA-13011.

19. The method of claim 9 further comprising contacting an ATCC accession No. PTA-13011 cell with said sample having a known amount of translation initiation inhibitory activity for a time and at a temperature effective to inhibit proliferation of said cell, and
   measuring the level of inhibition of proliferation of said ATCC accession No. PTA-13011 cell induced by said sample,
   wherein if said sample inhibits the proliferation of said ATCC accession No. PTA-13011 cell, the-sample does not contain translation initiation inhibitory activity.

* * * * *